(12) United States Patent
Furnish et al.

(10) Patent No.: US 7,742,805 B2
(45) Date of Patent: Jun. 22, 2010

(54) OPTICAL CATHETER WITH DUAL-STAGE BEAM REDIRECTOR

(75) Inventors: Simon Furnish, New York, NY (US); Andres F. Zuluaga, Boston, MA (US)

(73) Assignee: InfraReDx, Inc., Burlington, MA (US)

( * ) Notice: Subject to any disclaimer, the term of this patent is extended or adjusted under 35 U.S.C. 154(b) by 834 days.

(21) Appl. No.: 10/655,671

(22) Filed: Sep. 5, 2003

(65) Prior Publication Data

US 2005/0054934 A1 Mar. 10, 2005

(51) Int. Cl.
*A61B 5/00* (2006.01)
(52) U.S. Cl. .................. 600/478; 600/476; 356/451
(58) Field of Classification Search ......... 600/473–479; 356/477, 479, 451
See application file for complete search history.

(56) References Cited

U.S. PATENT DOCUMENTS

| | | | |
|---|---|---|---|
| 3,494,354 A | | 2/1970 | Yokota et al. |
| 4,195,904 A | * | 4/1980 | Yamashita .................. 359/367 |
| 4,398,811 A | | 8/1983 | Nishioka et al. |
| 5,304,173 A | * | 4/1994 | Kittrell et al. ................. 606/15 |
| 5,318,024 A | * | 6/1994 | Kittrell et al. ............... 600/478 |
| 6,137,938 A | | 10/2000 | Korn et al. |
| 6,304,688 B1 | | 10/2001 | Korn et al. |
| 6,701,181 B2 | * | 3/2004 | Tang et al. .................. 600/478 |
| 6,718,088 B2 | * | 4/2004 | Okazaki et al. ............... 385/27 |
| 2003/0191398 A1 | * | 10/2003 | Motz et al. .................. 600/478 |
| 2004/0034290 A1 | * | 2/2004 | Zuluaga ....................... 600/310 |
| 2004/0077950 A1 | * | 4/2004 | Marshik-Geurts et al. ... 600/475 |
| 2004/0111032 A1 | * | 6/2004 | Korn ............................ 600/478 |
| 2004/0249289 A1 | * | 12/2004 | Zuluaga et al. ............... 600/473 |
| 2005/0020926 A1 | * | 1/2005 | Wiklof et al. ................ 600/476 |
| 2007/0038119 A1 | * | 2/2007 | Chen et al. ................... 600/476 |
| 2007/0038123 A1 | * | 2/2007 | Fulghum ...................... 600/476 |

FOREIGN PATENT DOCUMENTS

| | | |
|---|---|---|
| JP | 53-105884 | 8/1978 |
| WO | WO 02/096478 | 12/2002 |
| WO | WO 02/096484 | 12/2002 |

OTHER PUBLICATIONS

Barber et al., "Ultrasonic Duplex Echo-Doppler Scanner," *IEEE Transactions on Biomedical Engineering*, vol. BME-21, No. 2, pp. 109-113 (Mar. 1974).
Bow et al., "Cardiac Imaging with a Real-Time Ultrasonic Scanner of a Rotating Transducer Design," *Proceedings of the British Medical Ultrasound Society*, p. 645 (Aug. 1978).
"Coronary-Artery Bypass Surgery," *The Lancet*, pp. 264-265 (Feb. 4, 1978).

(Continued)

*Primary Examiner*—Brian Casler
*Assistant Examiner*—Amanda Lauritzen
(74) *Attorney, Agent, or Firm*—Rothwell, Figg, Ernst & Manbeck, P.C.

(57) ABSTRACT

A catheter includes separate first and second optical channels extending between proximal and distal portion thereof. First and second beam redirectors in optical communication with the respective first and second optical channels each have on-axis stage and an off-axis stage.

18 Claims, 7 Drawing Sheets

OTHER PUBLICATIONS

Hisanaga et al., "High Speed Rotating Scanner for Transesophageal Cross-Sectional Echocardiography," *The American Journal of Cardiology*, vol. 46, pp. 837-842 (Nov. 1980).

Lancée et al., "Construction of a circular ultrasonic array with miniature elements for cardiac application," Thorax Center, Department of Echocardiography and Central Research Workshop, Erasmus University, Rotterdam, The Netherlands, pp. 49-53 (undated).

Martin et al., "An Ultrasonic Catheter Tip Instrument for Measuring Volume Blood Flow," Departments of Anesthesiology & Bioengineering, University of Washington, Seattle, Washington, pp. 13-17 (undated).

Martin et al., "Ultrasonic Catheter Tip Instrument for Measurement of Vessel, Cross-Sectional Area," 27th ACEMB, Marriott Hotel, Philadelphia, Pennsylvania, p. 186 (Oct. 6-10, 1974).

Martin and Watkins, "An Ultrasonic Catheter for Intravascular Measurement of Blood Flow: Technical Details," *IEEE Transactions on Sonics and Ultrasonics*, vol. SU-27, No. 6, pp. 277-286 (Nov. 1980).

Pérez et al., "Applicability of Ultrasonic Tissue Characterization for Longitudinal Assessment and Differentiation of Calcification and Fibrosis in Cardiomyopathy," *American College of Cardiology*, vol. 4, No. 1, pp. 88-93 (Jul. 1984).

Tomoike et al., "Continuous measurement of coronary artery diameter in situ," *American Physiological Society*, pp. H73-H79 (undated).

Van Orden et al., "A technique for monitoring blood flow changes with miniaturized Doppler flow probes," *American Physiological Society*, pp. H1005-H1009 (undated).

Ycas and Barnes, "An Ultrasonic Drill for Cleaning Blood Vessels," Department of Electrical Engineering, University of Colorado, Boulder, Colorado, pp. 165-167 (undated).

Office Action dispatched Feb. 9, 2010 in Japanese patent application No. 2006-525424 (4pp.) and English translation thereof (4 pp.).

* cited by examiner

OPTICAL CATHETER WITH DUAL-STAGE BEAM REDIRECTOR

FIELD OF INVENTION

This invention relates to catheters, and in particular, to optical catheters.

BACKGROUND

Vulnerable plaques are lipid filled cavities that form within the wall of an artery. These plaques, when ruptured, can cause massive clotting in the artery. The resultant clot can interfere with blood flow to the brain, resulting in a stroke, or with blood flow to the coronary arteries, resulting in a heart attack.

To locate vulnerable plaques, one inserts a catheter through the lumen of the artery. The catheter includes a delivery fiber for illuminating a spot on the arterial wall and a collection fiber for collecting scattered light that results from that illumination. The delivery fiber and the collection fiber form distinct optical channels within the catheter.

Light propagating on the delivery fiber travels axially, along the axis of the catheter. A delivery mirror intercepts this light and directs it radially outward so that it illuminates an illumination spot on the arterial wall. A collection mirror intercepts light scattered from inside the arterial wall and directs it axially, into the collection fiber.

The collection mirror is disposed or oriented such that the scattered light is received from a collection zone that is separate from the illumination zone. This minimizes glare resulting from specular reflection from the arterial wall.

SUMMARY

The invention is based on the recognition that dividing the task of beam redirection into two stages, one for deflecting the collection and delivery beams by small, but different angles, and the other for performing gross beam deflections, results in a simpler and more compact distal portion of a catheter.

In one aspect, the invention includes a catheter having separate first and second optical channels extending between proximal and distal portion thereof. First and second beam redirectors in optical communication with the respective first and second optical channels each have on-axis stage and an off-axis stage.

In one embodiment, the first and second beam redirectors share the same off-axis stage. The off-axis stage can be, for example, a mirror or a prism in optical communication with both the first and second optical channels.

In another embodiment, the first optical channel includes a first core of an optical fiber, and the second optical channel includes a second core of the optical fiber, the first and second core being spaced apart from each other.

Alternatively, the first channel can includes a first set of cores in an optical fiber, and the second channel includes a second set of cores in the optical fiber. In such a case, the on-axis stage of the first beam redirector can include a first subaperture of a lens, and the on-axis stage of the second beam redirector can include a second subaperture of the lens. The first and second subapertures are in optical communication with the first and second sets of cores respectively.

In another embodiment, the first set of cores includes a central core coincident with an axis of the fiber, and the second set of cores includes a set of peripheral cores circularly disposed around the central core. In such a case, the on-axis stage of the first beam redirector includes a central subaperture of a lens and the on-axis stage of the second beam redirector includes a peripheral subaperture of the lens. The central subaperture is in optical communication with the central core and the peripheral subaperture is in optical communication with the peripheral cores.

In another embodiment, the first set of cores intersects a first portion of a distal face of the fiber and the second set of cores intersects a second portion of the distal face. The first and second portions intersect so as to define a face angle relative to each other.

In another embodiment, the first channel includes a first set of optical fibers and the second channel includes a second set of optical fibers. In such a case, the first set of optical fibers can include a central fiber coincident with an axis of the catheter, and the second set of optical fibers can include a plurality of peripheral fibers circularly disposed about the central fiber.

Another aspect of the invention includes a multi-channel optical redirector having first and second beam redirectors for placement in optical communication with a first and second optical channels. Both the first and second beam redirectors have an on-axis stage and an off-axis stage.

The invention also includes a system for identifying vulnerable plaque. The system has a catheter, a light source, and a detector. The catheter has separate first and second optical channels extending between a proximal an distal portion thereof. First and second beam redirectors in optical communication with the respective first and second optical channels each have at least an on-axis stage and an off-axis stage. The light source directs light into the first optical channel, and the detector detects light from the second optical channel.

The invention also includes a method for collecting light from a wall of a lumen by passing a delivery beam into a delivery channel extending along the lumen; deflecting the delivery beam; directing the delivery beam toward the wall; receiving a collection beam from the wall; directing the collection beam toward a collection channel; and deflecting the collection beam into the collection channel.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
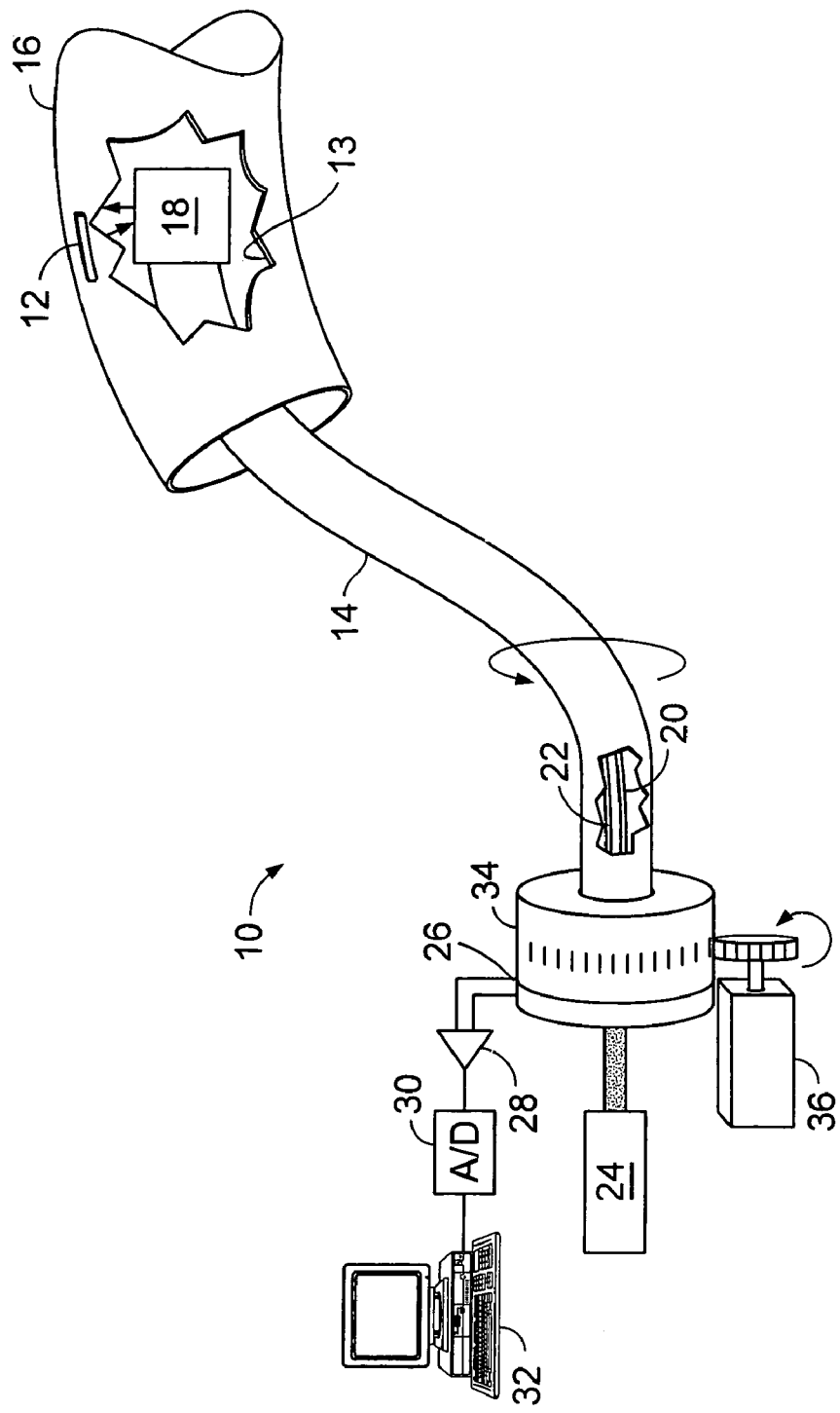
FIG. 1 is a schematic illustration of a system for identifying vulnerable plaque.

FIG. 1 shows a diagnostic system 10 for identifying vulnerable plaque 12 in an arterial wall 13 of a patient. The diagnostic system 10 features a catheter 14 to be inserted into a selected artery 16, e.g. a coronary artery, of the patient. A distal aperture portion 18 of the catheter 14 is transparent to light of the near-infrared or infrared wavelengths used by the diagnostic system 10. As used herein, the term "infrared" is intended to cover both of these cases.

At least two optical channels, a delivery channel 20 and a collection channel 22, extend along the catheter 14. The optical channels can be realized by providing a single fiber having separate cores. Alternatively, the optical channels can be realized by providing separate optical fibers. Each channel 20, 22 can be formed by a single core or fiber, or by a plurality of cores and/or fibers. As used herein, the term "channel" need not be restricted to a single physical structure. For example, a plurality of fibers, or a plurality of cores within a fiber, can collectively function as the "channel."

The delivery channel 20 delivers light from a light source 24 to an off-axis redirector at the distal end of the catheter 14. The off-axis redirector intercepts the axially directed beam carried by the delivery channel 20 and redirects it radially outward toward the distal aperture portion 18, where it exits the catheter 14 and proceeds toward the arterial wall 13. Exemplary off-axis redirectors include mirrors and prisms, and, in particular, right-angle mirrors and prisms.

The collection channel 22 collects light scattered from within the arterial wall 13. The off-axis redirector intercepts scattered light entering the catheter 14 through the distal aperture portion 18 and redirects that scattered light into the collection channel 22. The collection channel 22 then guides the scattered light, referred to herein as the "collection beam," to a detector 26 coupled to its proximal end.

The detector 26 provides an electrical signal indicative of light intensity to an amplifier 28 connected to an analog-to-digital ("A/D") converter 30. The A/D converter 30 converts this signal into data that can be analyzed by a data processing system 32 to identify the presence of a vulnerable plaque 12 hidden beneath the arterial wall 13.

A rotary coupler 34 driven by a motor 36 engages the proximal end of the catheter 14. As the motor 36 spins the catheter 14, light exiting the catheter 14 sweeps a circumferential path around the arterial wall 13. This feature enables the diagnostic system 10 to circumferentially scan the arterial wall 13 with an illumination spot and to collect scattered light from an annular collection zone that surrounds the illumination spot.

In addition to spinning the catheter 14, the rotary coupler 34 guides light from the light source 24 into the proximal end of the delivery channel 20 and guides light emerging from the proximal end of the collection channel 22 into the detector 26.

Figure 2:
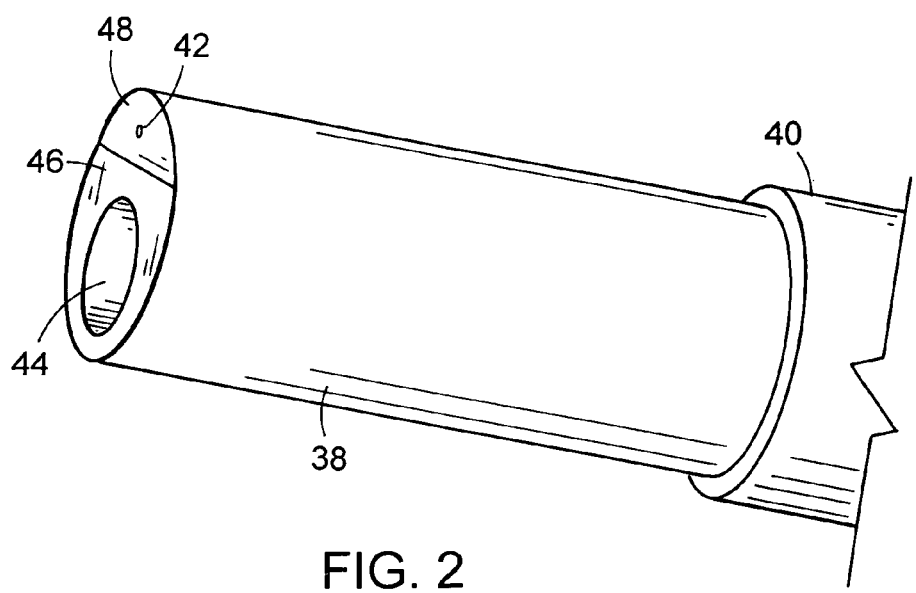
FIG. 2 is a cut-away view of a collection channel and delivery channel integrated into a single optical fiber.

FIG. 2 shows an optical fiber 38 that extends through the catheter 14. The cladding 40 covering the distal tip is removed to show an eccentric core 42 and a central core 44 integrated into the same optical fiber 38. In FIG. 2, the eccentric core 42 provides the delivery channel 20 and the central core 44 provides the collection channel 22. The distal tip of the fiber 38 is polished to form a collection face 46 and a delivery face 48 that form a face angle relative to each other.

The face angle deflects the collection beam relative to the delivery beam, thereby providing separation between the illumination spot and the collection zone. In some embodiments, the delivery face 48 and the collection face 46 both form an angle relative to a transverse plane of the fiber. However, in other embodiments, a face angle can also be achieved by having only one of the delivery and collection faces 56, 48 form an angle relative to the transverse plane.

Figure 3A:
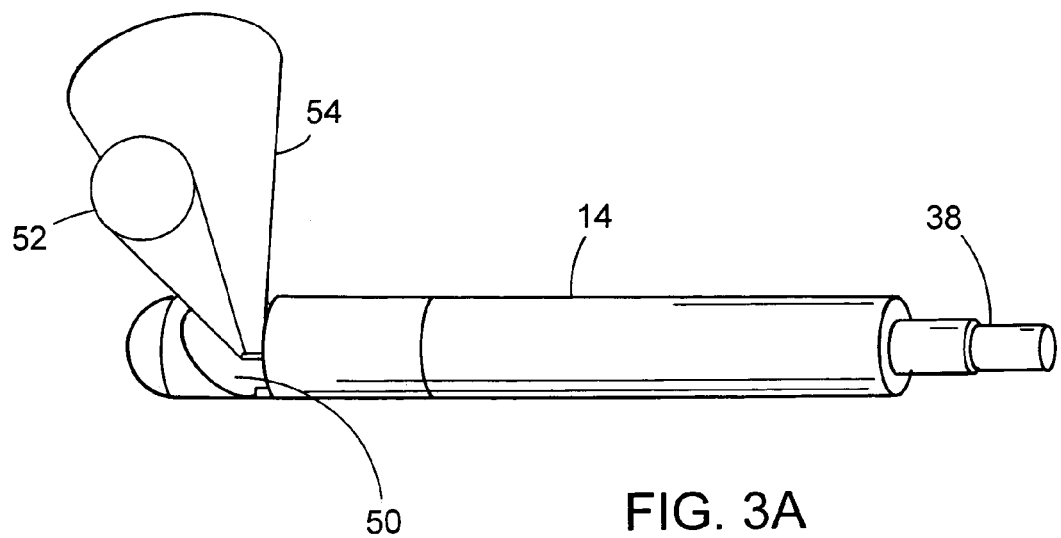
FIGS. 3A and 3B show delivery and collection beams formed by a catheter incorporating the fiber of FIG. 2.
Figure 3B:
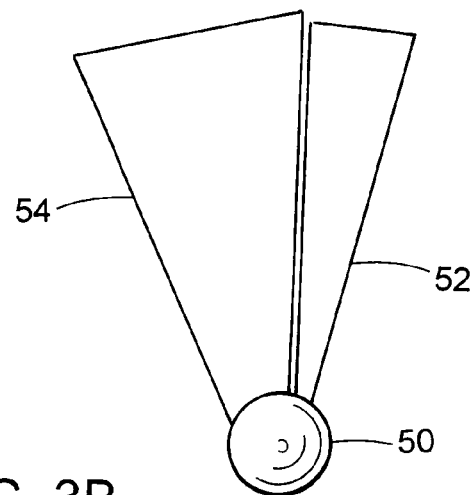

The collection channel 22 and the delivery channel 20 are in communication with an off-axis redirector 50, disposed at the distal tip of the catheter 14, as shown in FIG. 3A. The off-axis redirector 50 re-directs an axially traveling delivery beam 52 on the delivery channel 20 radially outward. The same off-axis redirector 50 re-directs the radially traveling collection beam 54 axially into the collection channel 22. Because the collection channel 22 and the delivery channel 20 are spaced apart, the collection beam 54 and the delivery beam 52 are already spatially separated from each other, as shown in FIGS. 3A and 3B. The extent of this separation, however, is limited by the extent to which the collection and delivery channel 20 can be spatially separated. The face angle enables this spacing to be further increased without the need to further separate the collection and delivery channels 20, 22.

An advantage of the configuration shown in FIG. 2 and FIGS. 3A-B is that only a single off-axis redirector 50 is required. In effect, the configuration features a two-stage delivery beam redirector and a two-stage collection beam redirector that share the same off-axis redirector 50. Each redirector includes a polished distal face (either the collection face 46 or the delivery face 48), which forms an on-axis redirector, and an off-axis redirector 50, formed, for example, by a right-angle mirror or prism. The angle made by the polished distal face 46, 48 introduces a small transverse deflection in the predominantly axial direction of the beam. This initial transverse deflection provided by the on-axis redirector is the first stage of the redirection. The second stage of the beam redirection is performed by the common off-axis redirector 50, which causes the predominantly axial beam to travel in a predominantly radial direction.

Figure 4A:
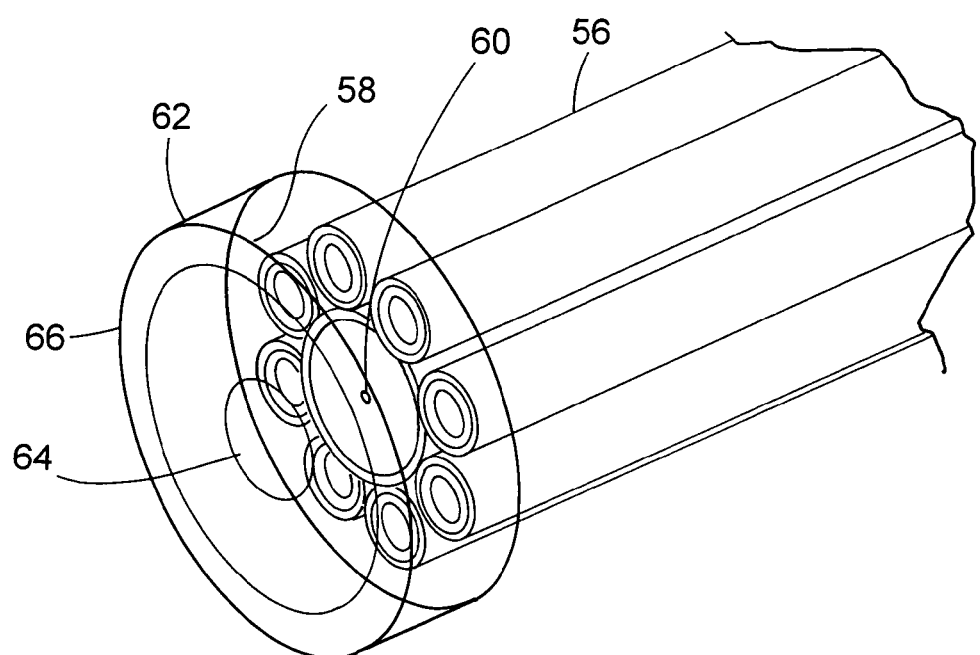
FIG. 4A is a schematic view of an embodiment in which the collection and delivery channels are made up of different optical fibers.

An additional embodiment, shown in FIG. 4A, features a plurality of collection fibers 56 circumferentially disposed on a cylindrical support 58 structure around a central delivery fiber 60. The collection fibers 56 collectively form the collection channel 22, and the central delivery fiber 60 forms the delivery channel 20.

Figure 4B:
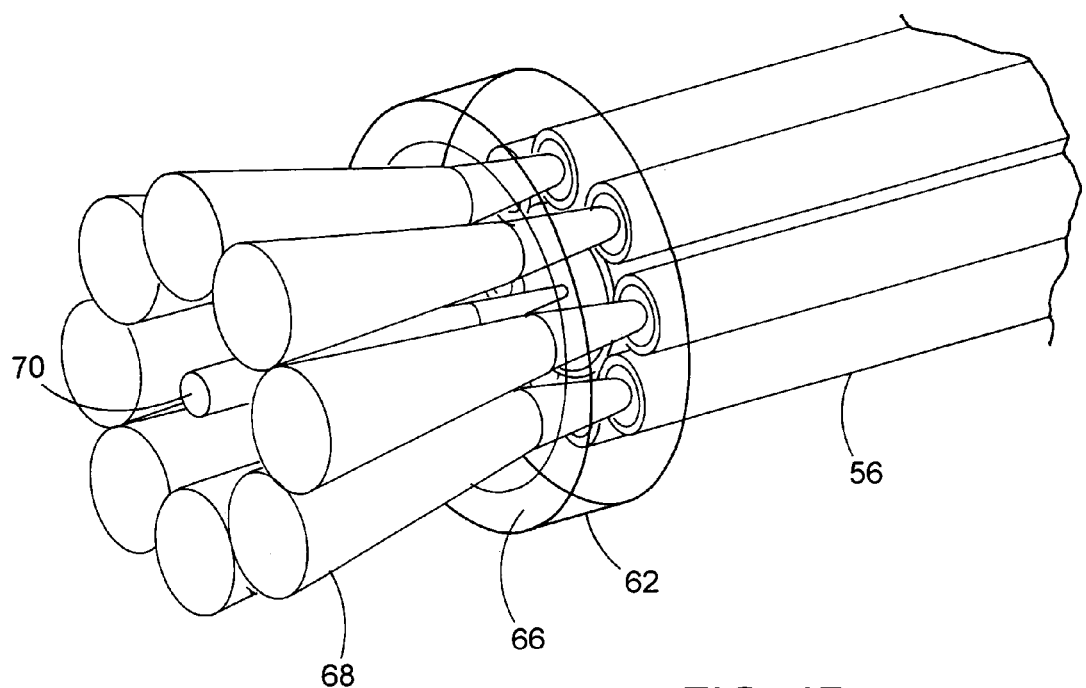
FIGS. 4B and 4C show delivery and collection beams formed by a catheter incorporating the fiber of FIG. 4A.

A lens 62 includes a central aperture 64 in optical communication with the delivery fiber 60 and a peripheral aperture 66 in optical communication with the collection fibers 56. As shown in FIG. 4B, the peripheral aperture 66 of the lens 62 provides an initial transverse deflection of the collection beams 68, as did the collection face 46 in the embodiment of FIGS. 2 and 3. Similarly, the central aperture 64 of the lens 62 provides an initial transverse deflection of the delivery beam 70. In the illustrated embodiment, the deflection is essentially zero. However, in general, this need not be the case.

Figure 4C:
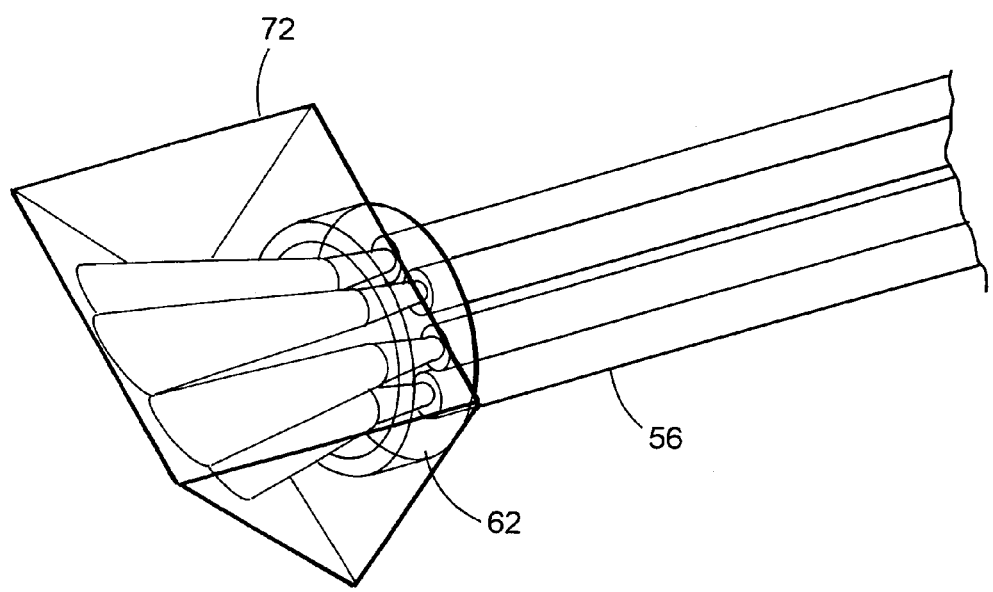

The central aperture 64 and the peripheral aperture 66 form the on-axis stages for two-stage delivery and collection redirectors. As was the case in FIGS. 2 and 3A-C, a common right-angle mirror or right-angle prism 72, shown in FIG. 4C, provides the second, or off-axis stage of the delivery and collection redirectors.

FIG. 4B shows the single delivery beam 70, as it emerges from the centrally disposed delivery fiber 60, and the plurality of collection beams 68, as they enter the collection fibers 56 circumferentially disposed about the delivery fiber 60. As is apparent from FIG. 4B, the peripheral aperture 66 of the lens 62 provides an initial outward transverse deflection to the collection beams 68, thereby separating them further from the delivery beam 70.

Light re-entering the lumen after having been scattered from a particular depth tends to re-enter the lumen by crossing the arterial wall 13 in an annular zone having the illumination spot at its center. An advantage of the embodiment shown in FIGS. 4A-C is that the resulting collection zone is also an annular zone having the illumination spot at its center. The embodiment of FIGS. 4A-C is therefore particularly efficient at collecting the available scattered light scattered from a particular depth.

The depth from which light has been scattered depends approximately on the radius of the annular zone. As a result, the extent to which the lens 62 provides a transverse deflection to the collection beams 68 controls the depth from which the collection channel 22 will collect scattered light.

Figure 5:
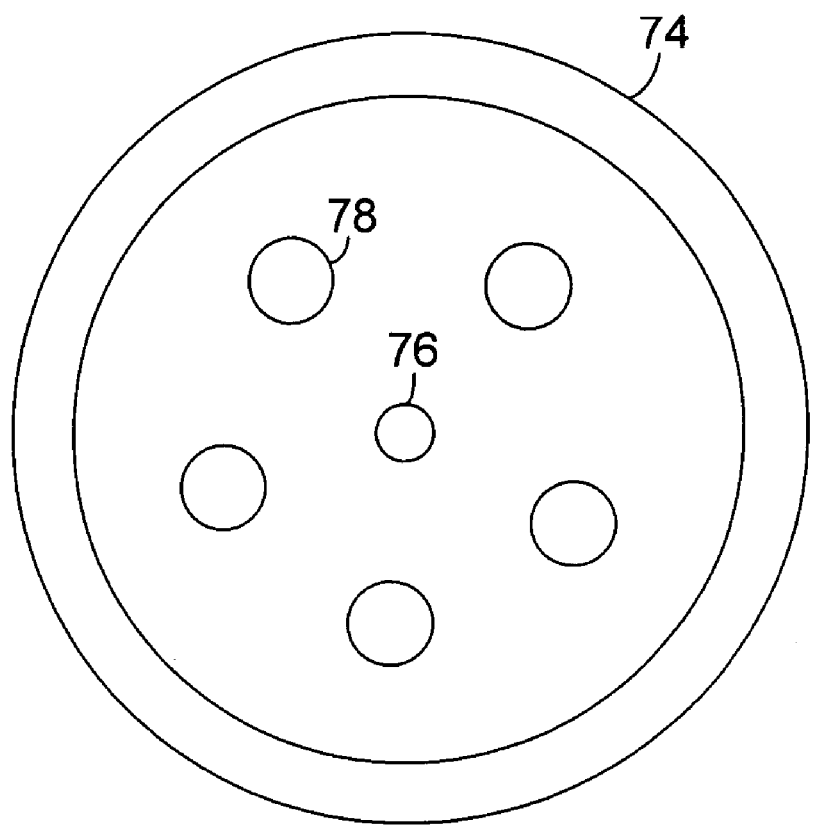
FIG. 5 is a cross section of an optical fiber having a multi-core collection channel and a single core delivery channel.

The embodiment shown in FIGS. 4A-C includes multiple collection fibers 56 that collectively make up a collection channel 22. However, in an alternative embodiment, a cross-section of which is shown in FIG. 5, a single optical fiber 74 can have multiple cores, one of which is a delivery core 76 at the center of the fiber 74. The remaining cores, which are collection cores 78, are circumferentially disposed about the central delivery core 76. This embodiment includes all the advantages of that in FIGS. 4A-C, with the additional advantage of being more compact and easier to construct.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A catheter comprising:
a first optical channel extending between a proximal and distal portion of the catheter;
a second optical channel extending between the proximal and distal portions of the catheter, the second optical channel being separate from the first optical channel;
a first beam redirector in optical communication with the first optical channel, the first beam redirector comprising a first stage and a second stage; and
a second beam redirector in optical communication with the second optical channel, the second beam redirector comprising a third stage and a fourth stage,
wherein the first stage is configured to receive a light beam from the first optical channel and to change a propagation direction of the light beam by refracting the light beam at a first non-zero angle with respect to an axis of the first optical channel; and
wherein the second stage is configured to receive the refracted light beam and to change a propagation direction of the refracted light beam by redirecting the refracted light beam at a second non-zero angle with respect to the axis of the first optical channel, the second angle being greater than the first angle.

2. The catheter of claim 1, wherein the second and fourth stages correspond to a shared common stage.

3. The catheter of claim 2, wherein the second stage comprises at least one of a mirror and a prism in optical communication with both the first and second optical channels.

4. The catheter of claim 1, wherein the second stage comprises at least one of a mirror and a prism in optical communication with the first optical channel.

5. The catheter of claim 1, wherein the first stage comprises a lens in optical communication with the first optical channel.

6. The catheter of claim 1, wherein the first optical channel comprises a first core of an optical fiber, and the second optical channel comprises a second core of the optical fiber, the first and second cores being spaced apart from each other.

7. The catheter of claim 1, wherein
the first optical channel comprises a first set of cores in an optical fiber, and
the second optical channel comprises a second set of cores in the optical fiber.

8. The catheter of claim 7, wherein
the first stage comprises a first subaperture of a lens, the first subaperture being in optical communication with the first set of cores, and
the third stage comprises a second subaperture of the lens, the second subaperture being in optical communication with the second set of cores.

9. The catheter of claim 7, wherein the first set of cores comprises a central core coincident with an axis of the fiber, and the second set of cores comprises a set of peripheral cores circularly disposed around the central core.

10. The catheter of claim 9, wherein
the first stage comprises a central subaperture of a lens, the central subaperture being in optical communication with the central core, and
the third stage comprises a peripheral subaperture of the lens, the peripheral subaperture being in optical communication with the peripheral cores.

11. The catheter of claim 7, wherein the first set of cores intersects a first portion of a distal face of the fiber and the second set of cores intersects a second portion of the distal face, the first and second portions defining a face angle relative to each other.

12. The catheter of claim 1, wherein the first optical channel comprises a first set of optical fibers and the second optical channel comprises a second set of optical fibers.

13. The catheter of claim 12, wherein the first set of optical fibers comprises a central fiber coincident with an axis of the catheter, and the second set of optical fibers comprises a plurality of peripheral fibers circularly disposed about the central fiber.

14. The system of claim 1, further comprising a rotary coupler coupled to the catheter.

15. The catheter of claim 1, wherein the third stage is configured to change a propagation direction of a light beam by redirecting the light beam at a third angle with respect to an axis of the second optical channel that is different from the first angle.

16. A multi-channel optical redirector comprising:
a first beam redirector for placement in optical communication with a first optical channel, the first beam redirector comprising a first stage configured to receive a light beam from the first optical channel and to change a propagation direction of the light beam by refracting the light beam at a first angle with respect to an axis of the first optical channel, and a second stage configured to receive the refracted light beam and to change a propagation direction of the refracted light beam by redirecting the refracted light beam at a second angle with respect to the axis of the first optical channel that is greater than the first angle; and
a second beam redirector for placement in optical communication with a second optical channel, the second beam redirector comprising a third stage configured to change a propagation direction of a light beam by redirecting the light beam at a third angle, and a fourth stage configured to change a propagation direction of a light beam by redirecting the light beam at a fourth angle that is greater than the third angle.

17. The multi-channel optical redirector of claim 16, wherein the third stage is configured to change a propagation direction of a light beam by redirecting the light beam at a third angle with respect to an axis of the second optical channel that is different from the first angle.

18. A system for identifying vulnerable plaque, the system comprising:
- a first optical channel extending between a proximal and distal portion of the catheter;
- a second optical channel extending between the proximal and distal portions of the catheter, the second optical channel being separate from the first optical channel;
- a first beam redirector in optical communication with the first optical channel, the first beam redirector comprising a first stage and a second stage;
- a second beam redirector in optical communication with the second optical channel, the second beam redirector comprising a third stage and a fourth stage;
- a light source for directing light into the first optical channel;
- a detector for detecting light from the second optical channel;
- wherein the first stage is configured to receive a light beam from the first optical channel and to change a propagation direction of the light beam by refracting the light beam at a first non-zero angle with respect to an axis of the first optical channel; and
- wherein the second stage is configured to receive the refracted light beam and to change a propagation direction of the refracted light beam by redirecting the refracted light beam at a second non-zero angle with respect to the axis of the first optical channel, the second angle being greater than the first angle.

* * * * *